US012805953B2

(12) United States Patent
Balicki et al.

(10) Patent No.: US 12,805,953 B2
(45) Date of Patent: Nov. 24, 2026

(54) CONTROL OF ROBOTIC ENDOVASCULAR DEVICES TO ALIGN TO TARGET VESSELS WITH FLUOROSCOPIC FEEDBACK

(71) Applicant: KONINKLIJKE PHILIPS N.V., Eindhoven (NL)

(72) Inventors: Marcin Arkadiusz Balicki, Cambridge, MA (US); Ayushi Sinha, Baltimore, MD (US)

(73) Assignee: Koninklijke Philips N.V., Eindhoven (NL)

( * ) Notice: Subject to any disclaimer, the term of this patent is extended or adjusted under 35 U.S.C. 154(b) by 280 days.

(21) Appl. No.: 18/708,107

(22) PCT Filed: Nov. 2, 2022

(86) PCT No.: PCT/EP2022/080485
§ 371 (c)(1),
(2) Date: May 7, 2024

(87) PCT Pub. No.: WO2023/083652
PCT Pub. Date: May 19, 2023

(65) Prior Publication Data
US 2026/0157810 A1 Jun. 11, 2026

Related U.S. Application Data

(60) Provisional application No. 63/277,721, filed on Nov. 10, 2021.

(30) Foreign Application Priority Data

Feb. 3, 2022 (EP) .................................... 22155023

(51) Int. Cl.
*A61B 34/20* (2016.01)
*A61B 34/30* (2016.01)
(Continued)

(52) U.S. Cl.
CPC ............. *A61B 34/32* (2016.02); *G16H 40/63* (2018.01); *A61B 2034/2065* (2016.02);
(Continued)

(58) Field of Classification Search
CPC ........... A61B 34/32; A61B 2034/2065; A61B 2034/303; A61B 2090/376; G16H 40/63; A61M 2025/0166
(Continued)

(56) References Cited

U.S. PATENT DOCUMENTS

| | | | | |
|---|---|---|---|---|
| 7,379,790 | B2 * | 5/2008 | Toth ...................... | A61B 34/30 901/33 |
| 7,991,105 | B2 | 8/2011 | Mielekamp et al. | |

(Continued)

FOREIGN PATENT DOCUMENTS

| | | | |
|---|---|---|---|
| CN | 111281544 | A | 6/2020 |
| EP | 3226800 | B1 | 10/2021 |

(Continued)

OTHER PUBLICATIONS

Ronneberger et al., "U-Net: Convolutional Networks for Biomedical Image Segmentation", May 18, 2015, vol. 1, pp. 1-8.

(Continued)

*Primary Examiner* — Jaime Figueroa

(57) ABSTRACT

A system controller (150) is arranged to control a robotic device (160) which drives motion of a first elongated device relative to a targeted vessel. The system controller (150) includes a memory (151) that stores instructions, a processor (152) that executes the instructions, and an image interface that receives data of a two-dimensional x-ray image and of the first elongated device in the two-dimensional x-ray image. When executed by the processor (152), the instructions cause the system controller (150) to control rotation of the first elongated device about a main longitudinal axis of
(Continued)

the first elongated device at a plurality of orientation angles, measure, from the data, a metric of the first elongated device at each of the plurality of orientation angles, identify an optimum orientation angle at which the metric is an extreme among the plurality of orientation angles; and control movement of the first elongated device at the optimum orientation angle into the targeted vessel.

21 Claims, 10 Drawing Sheets

(51) Int. Cl.
*A61B 34/32* (2016.01)
*G16H 40/63* (2018.01)
*A61B 90/00* (2016.01)
*A61M 25/01* (2006.01)

(52) U.S. Cl.
CPC ... *A61B 2034/303* (2016.02); *A61B 2090/376* (2016.02); *A61M 2025/0166* (2013.01)

(58) Field of Classification Search
USPC ................. 700/245–264; 318/568.11–568.25
See application file for complete search history.

(56) References Cited

U.S. PATENT DOCUMENTS

| | | | | |
|---|---|---|---|---|
| 8,218,846 | B2 * | 7/2012 | Trumer | A61B 6/5217 382/131 |
| 9,226,796 | B2 * | 1/2016 | Bowling | B25J 9/009 |
| 9,277,970 | B2 * | 3/2016 | Mansi | G06T 19/20 |
| 10,217,217 | B2 | 2/2019 | Dhruwdas | |
| 10,507,063 | B2 * | 12/2019 | Zuhars | A61B 34/20 |
| 10,679,758 | B2 * | 6/2020 | Fox | G16H 20/40 |
| 10,758,310 | B2 * | 9/2020 | Shelton, IV | G16H 40/63 |
| 10,932,863 | B2 * | 3/2021 | Adler | A61B 5/339 |
| 10,944,728 | B2 * | 3/2021 | Wiener | G16H 20/40 |
| 11,147,635 | B1 * | 10/2021 | Sganga | G16H 40/63 |
| 11,154,366 | B1 | 10/2021 | Sganga et al. | |
| 11,197,725 | B1 * | 12/2021 | Sganga | G16H 30/40 |
| 11,246,662 | B2 * | 2/2022 | Adler | A61B 34/10 |
| 11,497,564 | B2 * | 11/2022 | Dahdouh | A61B 34/35 |
| 2005/0251156 | A1 * | 11/2005 | Toth | G16H 40/40 606/153 |
| 2010/0204646 | A1 * | 8/2010 | Plicchi | A61B 34/30 604/95.01 |
| 2014/0022250 | A1 * | 1/2014 | Mansi | G06T 7/149 345/420 |
| 2016/0213884 | A1 | 7/2016 | Park | |
| 2017/0035514 | A1 * | 2/2017 | Fox | G06Q 10/10 |
| 2019/0038357 | A1 * | 2/2019 | Adler | A61B 34/10 |
| 2019/0038363 | A1 * | 2/2019 | Adler | A61B 5/339 |
| 2019/0038872 | A1 | 2/2019 | Destrebecq et al. | |
| 2021/0093406 | A1 * | 4/2021 | Blacker | A61B 34/25 |
| 2021/0393335 | A1 * | 12/2021 | Sganga | G16H 40/63 |
| 2021/0393336 | A1 * | 12/2021 | Sganga | A61B 34/25 |
| 2022/0202506 | A1 * | 6/2022 | Sganga | G16H 30/40 |

FOREIGN PATENT DOCUMENTS

| | | | |
|---|---|---|---|
| KR | 20200081224 | A | 7/2020 |
| WO | 2021011571 | A1 | 1/2021 |
| WO | 2022106377 | A1 | 5/2022 |
| WO | 2023089117 | A1 | 5/2023 |

OTHER PUBLICATIONS

Ambrosini et al., "Fully automatic and real-time catheter segmentation in X-ray fluoroscopy." International Conference on Medical Image Computing and Computer-Assisted Intervention. Springer, Cham, 2017, pp. 1-8.

Hinton et al., "Transforming Auto-Encoders", Artificial Neural Networks and Machine Learning—Department of Computer Science, (2011), pp. 44-51.

International Search report and Written Opinion of PCT/EP2022/080485, dated Feb. 8, 2023.

* cited by examiner

CONTROL OF ROBOTIC ENDOVASCULAR DEVICES TO ALIGN TO TARGET VESSELS WITH FLUOROSCOPIC FEEDBACK

CROSS-REFERENCE TO PRIOR APPLICATIONS

This application is the U.S. National Phase application under 35 U.S.C. § 371 of International Application No. PCT/EP2022/080485, filed on Nov. 2, 2022, which claims the benefit of European Patent Application No. 22155023.9, filed on Feb. 3, 2022, and U.S. Provisional Patent Application Ser. No. 63/277,721, filed on Nov. 10, 2021. These applications are hereby incorporated by reference herein.

BACKGROUND

Vascular passages are defined by delicate vascular walls. Endovascular devices are passed through vascular passages in endovascular interventional medical procedures, and constantly present risk of perforating the delicate vascular walls. Examples of endovascular devices include guidewires and catheters. In some endovascular interventional medical procedures, endovascular devices are navigated to treatment sites. A guidewire may be inserted endovascularly before a coaxial catheter is endovascularly guided along the guidewire to the treatment site. Medical imaging such as 2D perspective fluoroscopy may be used to provide image feedback to a skilled professional to assist in guiding the endovascular devices.

Precise manipulation of multiple coaxial endovascular devices such as guidewire/catheter combinations requires superb image interpretation ability and hand-eye coordination, both of which are typically the product of years of experience. Experienced professionals obtain skills through observation and trial and error over many years. However, endovascular navigation is not routine for novices, and presents difficulties even for experienced professionals in cases that are considered difficult due, for example, to tortuous anatomy. Skilled professionals are sometimes unavailable for emergencies such as stroke treatments, and the absence of required skills presents heightened risks of perforating the delicate vascular walls, which may sometimes prove fatal.

If a 3D model is used to navigate a guidewire in the right branch, additional radiation is required to obtain the 3D model. Additionally, tracking sensors may then have to be provided to the guidewire to track the 3D location of the guidewire. Moreover, some tracking sensors have to be provided in the guidewire to track its 3D location, which not only imposes constraints and costs, but may increase the thickness of the guidewire.

SUMMARY

A system controller is arranged to control a robotic device which drives motion of a first elongated device relative to a targeted vessel. The system controller includes one or at least one memory that stores instructions, one or at least one processor that executes the instructions, and an image interface that receives data of a two-dimensional x-ray image and of the first elongated device in the two-dimensional x-ray image. When executed by the processor, the instructions cause the system controller to control rotation of the first elongated device about a main longitudinal axis of the first elongated device at a plurality of orientation angles; measure, from the data, a metric of the first elongated device at each of the plurality of orientation angles, preferably such a metric being representative of an out-of-plane angle defined by the angle between a plane defined by the first elongated device and the plane of the image; identify at least one extreme orientation angle at which the metric is an extreme (metric) among the plurality of orientation angles; optionally identify or determined an optimum orientation angle from the extreme among the plurality of orientation angles (optionally the metric is an extreme among the plurality of orientation angles); and control movement of the first elongated device at this determined optimum orientation angle, preferably enter into or to face the targeted vessel, without (or with) retraction.

A system includes an X-ray imaging system configured to image anatomy of a subject and a first elongated device; a robotic device configured to control movement of the first elongated device, and a system controller. The system controller is configured to control rotation of the first elongated device about a main longitudinal axis of the first elongated device at a plurality of orientation angles; measure, from images captured by the X-ray imaging system, a metric of the first elongated device at each of the plurality of orientation angles, preferably such a metric being representative of an out-of-plane angle defined by the angle between a plane defined by the first elongated device and the plane of the image; identify at least one extreme orientation angle at which the metric is an extreme (metric) among the plurality of orientation angles; optionally identify or determine an optimum orientation angle from the extreme among the plurality of orientation angles (optionally the metric is an extreme among the plurality of orientation angles), and control movement of the first elongated device at this determined optimum orientation angle, preferably to enter into or face a targeted vessel, without (or with) retraction.

According to another aspect of the present disclosure, a method is implemented by a system controller which is arranged to control a robotic device that drives motion of a first elongated device relative to a targeted vessel. The method includes receiving, by an image interface of the system controller, data of a two-dimensional x-ray image and of the first elongated device in the two-dimensional x-ray image; controlling rotation of the first elongated device about a main longitudinal axis of the first elongated device at a plurality of orientation angles; measuring, from the data, a metric of the first elongated device at each of the plurality of orientation angles, preferably such a metric being representative of an out-of-plane angle defined by the angle between a plane defined by the first elongated device and the plane of the image; identifying at least one extreme orientation angle at which the metric is an extreme (metric) among the plurality of orientation angles; identifying or determining an optimum orientation angle from the extreme among the plurality of orientation angles (optionally the metric is an extreme among the plurality of orientation angles), and controlling movement of the first elongated device at the determined optimum orientation angle, preferably to enter into or to face the targeted vessel, without (or with) retraction.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
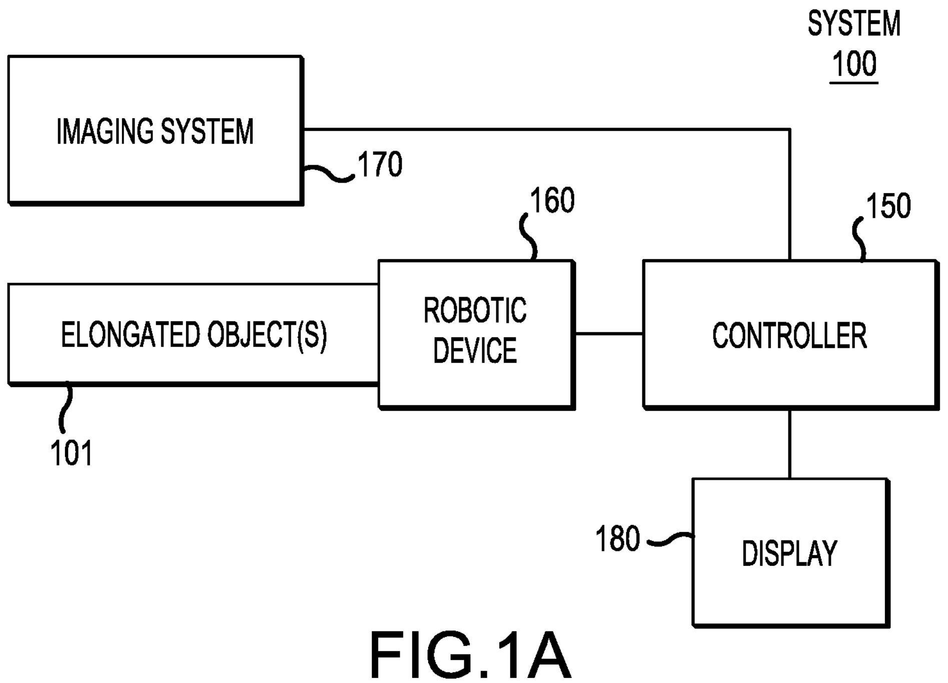
FIG. 1A illustrates a system for control of robotic endovascular devices to align to target vessels with fluoroscopic feedback, in accordance with a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, the invention may allow determining orientations of an elongated device navigated in a vascular system based on and from a fixed two-dimensional image and without any sensing elements or markers embedded in the device, based on metric(s) measured from the image data when the elongated device is controlled in rotation (preferably such a metric being representative of an out-of-plane angle which is the angle between the device plane (i.e. which is defined by, or in other words, including the elongated device) and the image plane. These orientation angles are of course of importance for the surgeon and/or the robot controlling the elongated device, to properly drive the elongated device through the vascular system. Thanks to the above-mentioned invention, reference orientations from the image plane can be found, including the orientation(s) corresponding to extreme metric(s)—the latter being necessarily associated with a known orientation of the device with respect to the image plane. In particular the use of a robot (to control the rotation of the elongated device in order to measure the various orientation angles according to the invention) allows finding this identification of extreme metric in an automatic, quick and accurately manner, appropriate with regard to surgery constraints (time, risks, reliability . . . ), without necessarily use of any sensors in the elongated device. In particular the invention allows a user (e.g. a surgeon) or the controller system to identify an optimum orientation towards the targeted vessel (or an optimum path of the elongated device to the targeted vessel), from the extreme metric previously identified and thus used as a reference orientation angle for identifying this optimum orientation angle with respect to the image plane. The optimum orientation angle may correspond to an orientation of the elongated device (or the distal portion or tip thereof) towards the targeted vessel (or another determined right pathway to the targeted vessel). Said identification of the optimum orientation angle (or an optimum directionality) may be entered by the user via a user interface or may be (semi-)automatically determined. Such identification of an optimum orientation angle of the elongated device may consider the presence, location and/or orientation of the targeted vessel. The presence, location and/or orientation of the targeted vessel may be determined by considering image elements in the image, surrounding the elongated device and including the targeted vessel. To that purpose an image processing may be implemented, including a segmentation step as well-known in the art, to identify in the two-dimensional image the presence, location and/or the orientation of the targeted vessel from the image plane. Use of a contrast agent may improve this image processing. Alternatively or in combination, determination of the presence, location and/or the orientation of the targeted vessel from the image plane, may involve the use of other two-dimensional image(s) previously acquired over different plane(s) including the elongated device, in the coordinate system of the imaging system acquiring the two-dimensional images, as well-known in the art. Alternatively or in combination, identification of the presence, location and/or the orientation of the targeted vessel from the image plane, may use of a previously acquired three-dimensional image (intra- or pre-operatively acquired), registered to the imaging system which acquires the two-dimensional image, as well-known in the art. Alternatively based control of robotic endovascular devices to align to target vessels with fluoroscopic feedback, in accordance with a representative embodiment as hereby described.

Said measured extreme metric(s) of the elongated device, which corresponds to known determined orientation angle (s) of the elongated device from the image plane (which may be also determined in an external coordinate system), is a clear reference for determining this optimum orientation angle with respect to the image plane (and so to the external coordinate system). And this is obtained without necessarily using sensors in the elongated device. Furthermore the invention may allow, in case the elongated device is positioned in a wrong branched vessel, to direct the elongated device to the (right) targeted vessel if adjacent, by a simple rotation without necessarily any retractation of it.

As described herein, fluoroscopic imaging may be synchronized with servo control of endovascular navigation devices to guide the endovascular navigation devices to anatomical targets. The synchronization between fluoroscopic imaging and servo control of endovascular navigation devices may be used to automatically identify optimum orientation angles at which the endovascular navigation devices can enter targeted vessel, without retraction.

FIG. 1A illustrates a system 100 for control of robotic endovascular devices to align to target vessels with fluoroscopic feedback, in accordance with a representative embodiment.

The system 100 in FIG. 1A is a system for control of robotic endovascular devices to align to target vessels with fluoroscopic feedback. The system 100 includes components that may be provided together or that may be distributed. The system 100 includes a system controller 150, a robotic device 160, an imaging system 170 and a display 180. The robotic device 160 is configured to drive elongated object(s) 101 under the control of the system controller 150 and based on images from the imaging system 170.

Before proceeding, it should be clear that the teachings herein are not limited to endovascular anatomy, though references herein are typically to endovascular anatomy and procedures. For example, anatomical targets may be ostiums which are part of fenestrated grafts and which are not necessarily vasculature anatomy. Procedures described herein may also involve other networks of anatomy, such as networks of tubular structures in lungs and livers.

The elongated object(s) 101 are representative of a first interventional device and a second interventional device which is coaxial with the first interventional device. The elongated object(s) 101 are endovascular navigation devices. An example of the elongated object(s) 101 is an inner device and an outer device, such as a guidewire sliding inside a catheter. The elongated object(s) 101 are driven by the robotic device 160 under the control of the system controller 150 and based on images of branched anatomy from the imaging system 170. The elongated object(s) 101 may include a main body along a main axis of the elongated object(s) 101 and a distal portion. The distal portion of either of the elongated object(s) 101 may be the portion at an end of the elongated object(s) 101 which is inserted first into the vascular system. For example, the distal portion may define a hook that is non-parallel to the main axis of the elongated object(s) 101 such that the elongated object(s) 101 define and primarily lie in a single plane ("device plane").

Figure 1B:
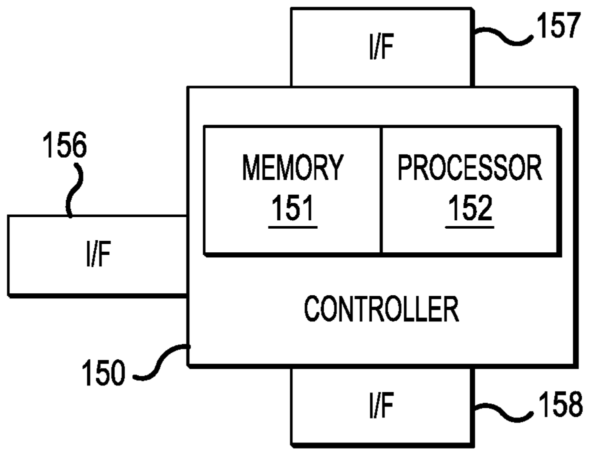
FIG. 1B illustrates a controller for control of robotic endovascular devices to align to target vessels with fluoroscopic feedback, in accordance with a representative embodiment.
Figure 9:
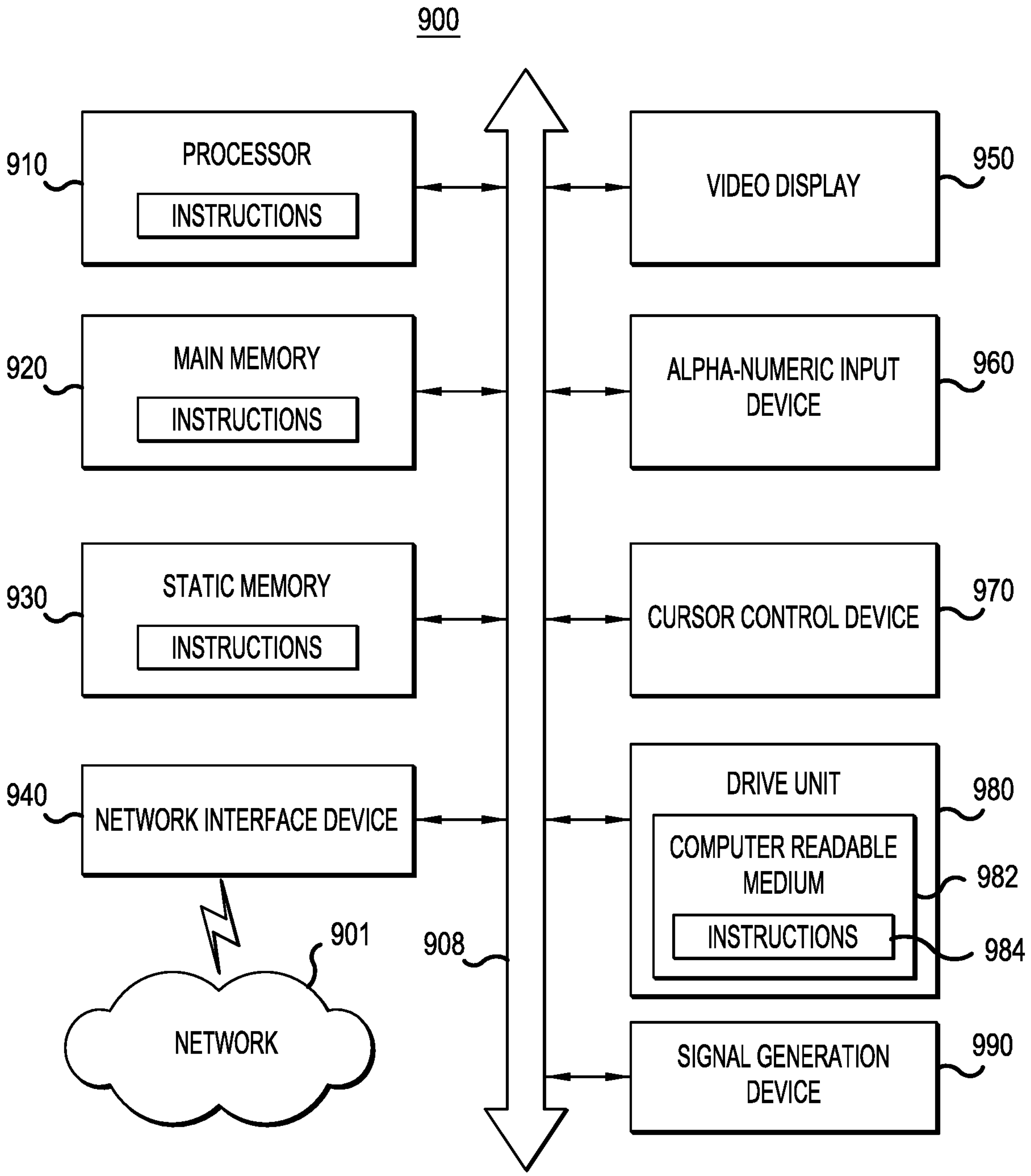
FIG. 9 illustrates a computer system, on which a method for control of robotic endovascular devices to align to target vessels with fluoroscopic feedback is implemented, in accordance with another representative embodiment.

The system controller 150 is further depicted in FIG. 1B, and includes at least a memory 151 that stores instructions and at least one processor 152 that executes the instructions. A computer that can be used to implement the system controller 150 is depicted in FIG. 9, though a system controller 150 may include more or fewer elements than depicted in FIG. 1B or in FIG. 9.

The system controller 150 is configured to detect operator input for a control mode, and plan and align the position of the imaging system 170 relative to the anatomical vessels of interest, such as to be parallel with the anatomical vessels of interest. The system controller 150 is also configured to analyze images from the imaging system 170 and parametrize features of the elongated object(s) 101 in the images from the imaging system 170. For example, the system controller 150 may use artificial intelligence (AI) to segment the elongated object(s) 101 in images from the imaging system 170.

The system controller 150 may create one or more goal reference metric(s) relative to one of the parameterized features of the elongated object(s) 101, or different goal reference metric(s) for multiple of the parameterized features of the elongated object(s) 101. The goal reference metric(s) serve as the basis for the system controller 150 to control the robotic device 60 to drive the elongated object(s) 101 to align the elongated object(s) 101 with the anatomical vessel to be cannulated, such as to drive the elongated object(s) 101 towards a portion of a targeted vessel such as an entrance to a branched targeted vessel. The system controller 150 may control the robotic device 160 to servo-drive the elongated object(s) 101 so that the metric of a parameterized feature from the images is minimized (or maximized) in the next image, or at least reduced (or increased) in the next image. The system controller 150 may control the driving by the robotic device 160 until the metric is at an extreme, or at least within a tolerance range set as one or more predetermined thresholds relative to an extreme, or when the operator deactivates control.

An example of a metric is a radius of curvature (in pixels) of the distal section of one of the elongated object(s) 101, such as when a fluoroscopic image shows a predetermined threshold or more of pixels as a radius of curvature of the distal section of one of the elongated object(s) 101. For example, the metric may reflect the curvature/radius of the distal portion with respect to a main axis of the elongated object(s) 101.

In controlling the robotic device 160 to drive the elongated object(s) 101, the system controller 150 may choose the image plane of the 2D image taken by the imaging system 170 so as to include a main axis of the portion of the targeted vessel towards which the elongated object(s) 101 are driven. That is, the system controller 150 may both control the robotic device 160 to drive the elongated object (s) 101 and control one or more functions of the imaging system 170. For example, a main branch of a vascular system may have a main axis which the system controller 150 ensures is in the 2D image taken by the imaging system 170. The distal portion of the elongated object(s) 101 may be non-parallel to the immediately adjacent portion of the elongated object(s) 101 extending in the vascular system along a main axis of the vascular system.

The system controller 150 may control the robotic device 160 to rotate the elongated object(s) 101 about the main axis of the elongated object(s) 101 to each of a plurality of orientation angles and obtain an image from the imaging system 170 at each of the orientation angles. The system controller 150 may measure metric(s) of the elongated object(s) 101 from the images taken at each orientation angle. The metric(s) may be representative of an out-of-plane angle which is the angle between the device plane (i.e., which is defined by the elongated object(s) 101) and the image plane (i.e., which is defined by the imaging system 170). When the elongated object(s) 101 has a maximum metric or minimum metric, it is possible also for the system controller 150 to indirectly estimate the parallel or perpendicular state or orientation angle of the elongated object(s) 101 relative to the image plane. The system controller 150 may identify when the metric(s) are at an extreme, or within or at a determined distance of an extreme, and select the corresponding orientation angle as the correct directionality for the robotic device 160 to drive the elongated object(s) 101. For example, the orientation angle corresponding to the smallest out-of-plane angle may be selected as the correct directionality for the elongated object(s) 101 to be driven. The system controller 150 may also command the robotic device 160 to drive the elongated object(s) 101 at the selected orientation angle into or towards the targeted vessel, with or without retraction. Said selection of the optimum orientation angle (or an optimum directionality) may be entered by a user (e.g. a surgeon) via an user interface or may be automatically, or semi-automatically (by requiring a user input to assist the computer processing), determined. Such selection of optimum orientation angle of the elongated object(s) 101 may consider the presence, location and/or orientation of the targeted vessel. The presence, location and/or orientation of the targeted vessel may be determined by considering image elements in the image, surrounding the elongated object(s) 101 and including the targeted vessel. To that purpose an image processing is implemented, including a segmentation step as well-known in the art. Use of a contrast agent may improve this image processing. Alternatively or in combination, determination of the presence, location and/or the orientation of the targeted vessel from the image plane, may involve the use of other two-dimensional image(s) previously acquired over different plane(s) including the elongated object(s) 101, in the coordinate system of the imaging system acquiring the two-dimensional images, as well-known in the art. Alternatively or in combination, identification of the presence, location and/or the orientation of the targeted vessel from the image plane, may use of a previously acquired three-dimensional image (intra- or pre-operatively acquired), registered to the imaging system which acquires the two-dimensional images, as well-known in the art.

The system controller 150 may also control the imaging system 170 to position so that the plane of the 2D image taken by the imaging system 170 lies in the cross-sectional plane of the entrance to the lumen (i.e., the ostium) of the targeted vessel, or so that the plane of the 2D image taken by the imaging system 170 is perpendicular to the perpendicular to a cross-section of the entrance to the lumen (i.e., the ostium) of the targeted vessel. This positioning of the imaging system 170 may be implemented before, during or after the measurement of the extreme metric and the selection of the optimum orientation angle. When the plane of the 2D image taken by the imaging system 170 is perpendicular to the distal portion of the elongated object(s) 101, the distal portion of the elongated object(s) 101 is fully out-of-plane of the imaging system 170, and this indication of perpendicularity may serve as a useful guide to control the robotic device 160 to drive the elongated object(s) 101 into the targeted vessel.

As a result of rotating the elongated object(s) 101 to multiple orientation angles until the metric(s) is/are at an extreme or within a predetermined distance of an extreme, tips of the elongated object(s) 101 may be automatically aligned with the entrance of targeted vessels at the optimum orientation angle. This optimum orientation angle is an extreme in the particular case that the plane of the 2D image is perpendicular to the ostium. The control by the system controller 150 may align the elongated object(s) 101 without performing any retraction or advancement of the elongated object(s) 101 into the targeted branch, and this reduces the risk of damaging the vascular walls.

The robotic device 160 is controlled by the system controller 150 to drive the motions of one or both of the elongated object(s) 101, and to rotate the elongated object(s) 101 about the main axis of the elongated object(s) 101 at multiple orientation angles. The robotic device 160 may control one or more degrees of freedom of control for one or both of the elongated object(s) 101. The robotic device 160 is configured to drive the elongated object(s) in one or more degrees of freedom, such as in three dimensions and about one or more axes. The robotic device 160 may include a servo motor used to drive the elongated object(s) 101 under the control of the system controller 150, and based on fluoroscopic feedback from the imaging system 170.

The imaging system 170 may be a fluoroscopic imaging system that captures fluoroscopic images of anatomy of a subject and the elongated object(s) 101 as the elongated object(s) 101 is/are inserted into the anatomy of the subject. The imaging system 170 may image the anatomy of the subject and the elongated object(s) 101 and may be movable directly by a user or under the control of the user via the system controller 150. The imaging system 170 may be an interventional X-ray imaging system. An interventional X-ray imaging system may include an X-ray tube adapted to generate X-rays and an X-ray detector configured to acquire time-series sequences of two-dimensional X-ray projection images such as fluoroscopy images. Examples of such X-ray imaging systems include digital radiography-fluoroscopy systems such as ProxiDiagnost from Philips, fixed C-arm X-ray systems such as Azurion from Philips, and mobile C-arm X-ray systems such as Veradius from Philips.

The display 180 may be local to the system controller 150 and may be connected to the system controller 150 via a local wired interface such as an Ethernet cable or via a local wireless interface such as a Wi-Fi connection. The display 180 is configured to display imaging content from the fluoroscopic images from the imaging system 170, along with the target datum and supplementary depictions of the elongated object(s) 101 relative to the target datum. The display 180 may be interfaced with other user input devices by which users can input instructions, including mouses, keyboards, thumbwheels and so on.

The display 180 may be a monitor such as a computer monitor, a display on a mobile device, a television, an electronic whiteboard, or another screen configured to display electronic imagery. The display 180 may also include one or more input interface(s) such as those noted above that may connect other elements or components to the system controller 150, as well as an interactive touch screen configured to display prompts to users and collect touch input from users. The display 180 may receive commands from the system controller 150 to display images of the elongated object(s) 101 at each orientation angle including the selected orientation angle corresponding to the extreme metric.

FIG. 1B illustrates system controller for control of robotic endovascular devices to align to target vessels with fluoroscopic feedback, in accordance with a representative embodiment.

The system controller 150 in FIG. 1B includes at least one memory 151, at least one processor 152, a first interface 156, a second interface 157, a third interface 158, and a fourth interface 159. The memory 151 stores instructions which are executed by the processor 152. The memory 151 may also store a library of controlling tools related to specific motions of the elongated object(s) 101. The processor 152 executes the instructions. The processor 152 may execute instructions to measure distances and/or orientations of the elongated object(s) 101 in the images and to parametrize the features of the elongated object(s) 101 in images. The analysis and parameterization by the processor 152 may be performed based on the branched anatomy surrounding the elongated object(s) 101 in the images, along with a predefined target in the anatomy in the images such as a target branch or intersection of branches in the images.

The interfaces of the system controller 150 include a first interface 156 to the robotic device 160, a second interface 157 to the imaging system 170, a third interface 158 to the display 180, and a fourth interface 159 to a user. The first interface 156, the second interface 157 and the third interface 158 may include ports, disk drives, wireless antennas, or other types of receiver circuitry.

The first interface 156 may be a data interface that received data from the robotic device 160 and that provides instructions to the robotic device 160. The second interface 157 may be an image interface that receives data of images and of the identified elongated object(s) 101 in the images from the imaging system 170. The elongated object(s) 101 may be identified in the images through artificial-intelligence based segmentation. The third interface 158 may be a data interface and an image interface that provides data and images to the display 180. The fourth interface 159 may include one or more user interfaces, such as a mouse, a keyboard, a microphone, a video camera, a touchscreen display, or other forms of interactive user interfaces. The fourth interface 159 may be a thumbwheel user interface used to allow the user to indicate the target point with a marking and direct the robotic device 160. The fourth interface 159 is therefore a user interface that receives user inputs, including inputs to set an operation mode for the robotic device 160 and inputs to make selections such as a selection of a predefined motion among multiple selectable options provided on the display 180.

The system controller 150 is configured to control the robotic device 160 to actuate the elongated object(s) 101 using fluoroscopic feedback from images from the imaging system 170. The system controller 150 may be provided as a stand-alone component as shown in FIG. 1B, or as a component of a device such as a workstation which also includes the display 180 in FIG. 1A. The system controller 150 may perform some of the operations described herein directly and may implement other operations described herein indirectly. For example, the system controller 150 may directly analyze fluoroscopic images from the imaging system 170 and may directly control the robotic device 160 to drive the elongated object(s) 101. The system controller 150 may indirectly control other operations such as by generating and transmitting content to be displayed on the display 180. Accordingly, the processes implemented by the system controller 150 when the processor 152 executes instructions from the memory 151 may include steps not directly performed by the system controller 150.

As an example, the system controller 150 may use encoded positional information, such as orientation, from the robotic device 160 to recall images corresponding to a current encoded position, from a previous sequence of images, to provide an estimated view of the elongated object(s) 101 in a secondary plane. The corresponding position of the robotic device 160 in the estimated secondary view provides additional spatial information about the location of the robotic device 160 relative to the target, and may be used to assist in the process of rotating the elongated object(s) 101, so as to rotate with fewer movements to fewer orientation angles in a shorter amount of time before an extreme metric is identified.

As another example, the system controller 150 may use a trained model (i.e., trained artificial intelligence) to predict views of the elongated object(s) 101 in a secondary plane. The model may use time-series sequences of two-dimensional projection images and input from the system controller 150 to predict whether a metric will be at an extreme at one or more orientation angles of the plurality of orientation angles. The prediction may be used to assist in the process of rotating the elongated object(s) 101, so as to rotate with fewer movements to fewer orientation angles in a shorter amount of time before the extreme metric is identified.

The system controller 150 may control the robotic device 160 to advance either or both of the elongated object(s) 101 to a location. Advancing is technically more complex than retraction due to the potential of interacting with tissue such as the vascular walls. Advancing automatically under the control of the robotic device 160 may be limited to advancing in a main anatomical branch to the entrance of a branch.

In some embodiments, the system controller 150 may control the robotic device 160 to align tips of the elongated object(s) 101 within a predetermined distance range (e.g., 5 pixels) of alignment. Alignment may be performed when a distance between the respective tips of the inner device and the outer device is outside of the predetermined distance range, such as by more than 5 pixels. The system controller 150 may control the robotic device 160 to rotate the elongated object(s) 101 once the tips are aligned. As yet another example, the system controller 150 may also control the robotic device 160 to retract the two elongated object(s) 101 once the tips are aligned. The elongated object(s) 101 may be retracted to a target point such as to an intersection between three branches.

The inner device or the outer device among the elongated object(s) 101 may be controlled by the robotic device 160 to rotate alone, separately and independently of the other of the outer device or the inner device of the elongated object(s) 101. The inner device or the outer device may be rotated to align the curvature of the ends of the elongated object(s) 101 based on the tangents of the tips of the elongated object(s) 101. For example, a user alert may be issued to the user, and the user may be prompted to rotate one of the inner device or the outer device of the elongated object(s). As another example, the inner device of the elongated object(s) 101 may be advanced by the robotic device 160 to a target point.

The system controller 150 may also advance the inner device by a distance past the outer device, so as to allow the retraction of the inner device due to retraction of the outer device. Advancing the inner device past the outer device may be performed when a user is retracting the outer device over a certain distance such that the inner device tends to be retracted with the outer device, which is not necessarily desirable. Therefore, the system controller 150 may servo-control the robotic device 160 to advance the inner device by a distance which offsets the retraction of the inner device with the retraction of the outer device. Advancing the inner device past the outer device may be based on the initial position of the tip of the inner device. In this way, the system controller 150 may anchor the inner device to an anatomical vessel/branch.

The system controller 150 may also provide suggestions on the display 180 for the user to show expected motions in a graphical sequence. The motions may be suggested using a trained prediction model based on past sequences of motions, along with the shape of the anatomy of the current subject, as well as the location of the target point in the anatomy of the current subject.

The system controller 150 may also provide servo-commands to the robotic device 160 based on the selection of one or more tools either automatically or based on input from the user via the fourth interface 159. The servo-commands may be communicated to the robotic device 160 via the first interface 156.

Figure 2:
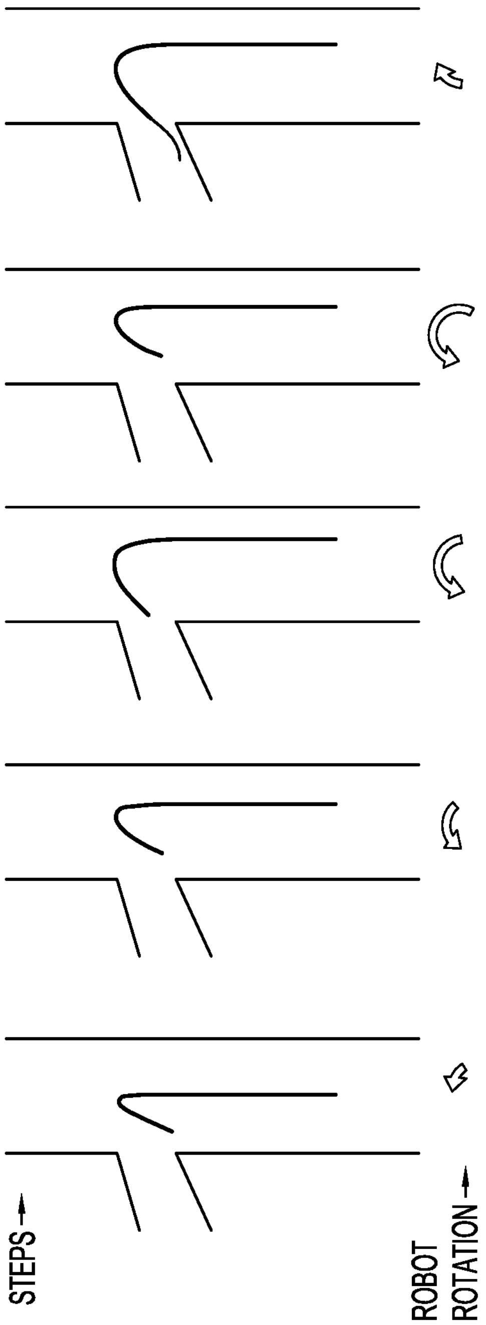
FIG. 2 illustrates a sequence of motions to align a catheter with a target vessel for cannulation, in accordance with a representative embodiment.

FIG. 2 illustrates a sequence of motions to align a catheter with a target vessel for cannulation, in accordance with a representative embodiment.

The sequence of motions in FIG. 2 is performed to improve endovascular intervention workflow by robotically assisting manipulation of the elongated object(s) 101 inside a branching vessel. The sequence is optimized using fluoroscopic imagery from the imaging system 170 combined with control of the robotic device 160 to drive/navigate the elongated object(s) 101.

The X-ray feedback is used to robotically and autonomously control the elongated object(s) 101. In FIG. 2, the elongated object(s) 101 may be, for example, a standard catheter and guidewire, which are navigated into vascular branches. As shown in FIG. 2, the catheter is disposed in the main vascular branch in each of five representations. The catheter has a main portion with a main axis aligned with the main axis of the main vascular branch, and a distal portion which is bent at the top of the main portion of the catheter. The elongated object(s) 101 are rotated until the distal end of the catheter is aligned in the direction of the target vessel that is in full projection to the view, as shown in FIG. 2.

In FIG. 2, the target vessel is automatically selected based on a surgical plan or is manually selected by the user, such as based on a corresponding angiogram or a registered 3D angiogram. The X-ray view of the imaging system 170 is adjusted so the target vessel axis is approximately parallel to the plane of the X-ray. The elongated object(s) 101 is/are servo-rotated automatically until the distal curved section is parallel to the view on the images from the imaging system 170, based on automatic visual inspection in the X-rays. The rotation in FIG. 2 may be automated, and may be triggered by user command such as by a user pressing a joystick button to improve usability. The sequence in FIG. 2 is independent of the shape of the elongated object(s) 101 so long as the elongated object(s) 101 are configured for intravascular use. The sequence in FIG. 2 is also applicable to elongated object(s) 101 which are steerable, along with elongated object(s) 101 which are driven under the control of the robotic device 160.

Figure 3A:
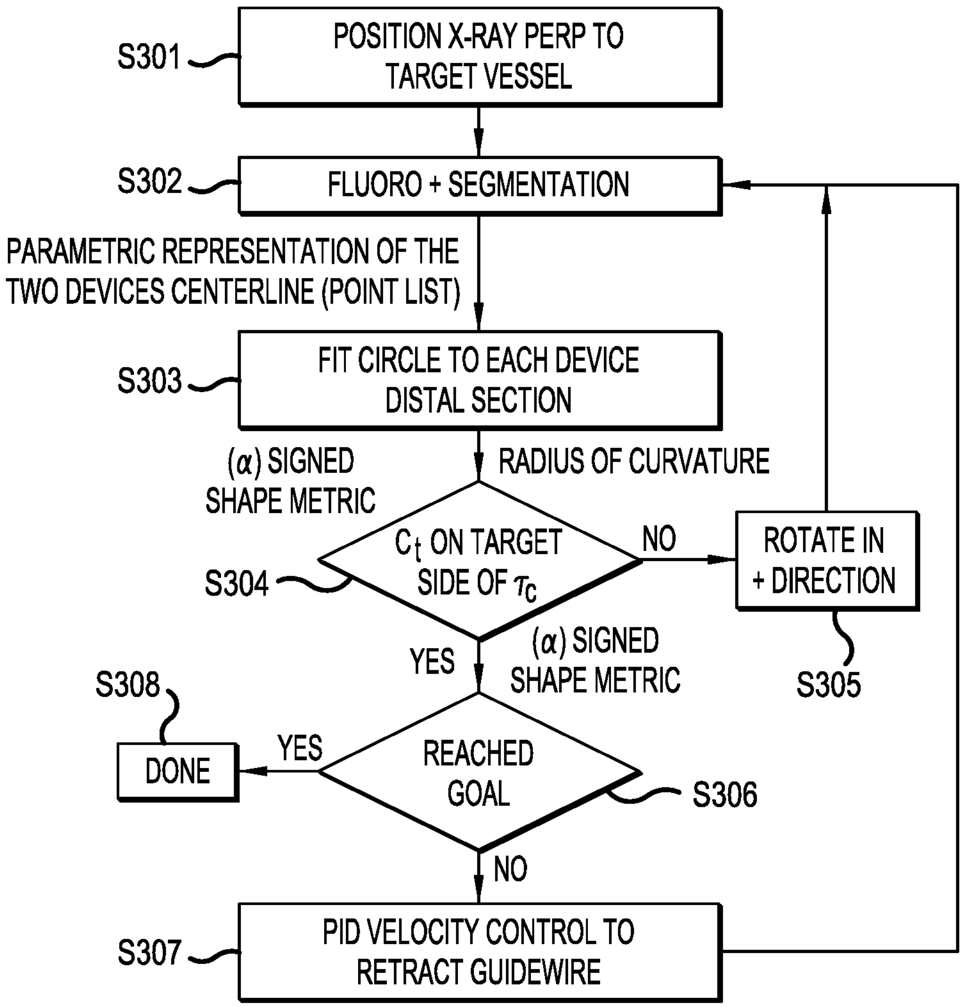
FIG. 3A illustrates a method for control of robotic endovascular devices to align to target vessels with fluoroscopic feedback, in accordance with a representative embodiment.
Figure 3B:
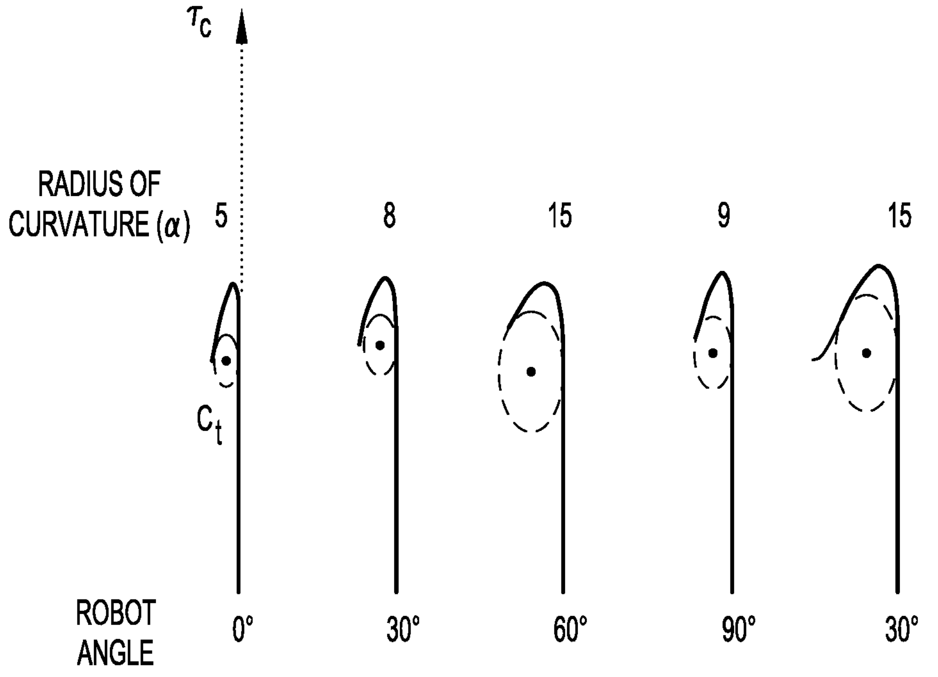
FIG. 3B illustrates a sequence of motions and a metric to align a catheter with a target vessel for cannulation, in accordance with the method of FIG. 3A.

FIG. 3A illustrates a method for control of robotic endovascular devices to align to target vessels with fluoroscopic feedback, in accordance with a representative embodiment. FIG. 3B illustrates a sequence of motions and a metric to align a catheter with a target vessel for cannulation, in accordance with the method of FIG. 3A.

The method of FIG. 3A may be performed by the system controller 150, or by the system 100 including the system controller 150. At S301 of FIG. 3A, the imaging system 170 is positioned perpendicular to a target vessel such that a plane of the two-dimensional image lies in a cross-section of an entrance of the targeted vessel. The imaging system 170 may be an X-ray imaging system so that the two-dimensional image is a two-dimensional X-ray image. The positioning may be directly by a user, or indirectly by the user instructing the system controller 150 to position the imaging system 170.

At S302, the imaging system 170 takes a fluoroscopic image, and sends the fluoroscopic image to the system controller 150 via the second interface 157. The elongated object(s) 101 in the fluoroscopic image are segmented by the system controller 150. Parametric representations of the elongated object(s) 101 may be provided as centerlines using line segments based on the segmentation. The segmenting from the fluoroscopic image taken at S302 is used to obtain the metric(s) described herein.

At S303, a circle is fit to the distal portion of each of the elongated object(s) 101 in the fluoroscopic image. The system controller 150 may obtain one or more signed shape metrics from the circle fit to the distal portion. As an example, the system controller 150 may obtain a radius of curvature of the circle fit to the distal portion as a signed shape metric. In another example embodiment, the distance of the center of the circle from the main device axis may be used.

At S304, the method of FIG. 3A includes determining whether the metric is at an extreme or within a predetermined range of an extreme. If not (S304=No), the system controller 150 commands the robotic device 160 to rotate the elongated object(s) 101 and returns to S302. If the metric is at an extreme or within a predetermined range of the extreme (S304=Yes), a determination at S306 is made as to whether the distal portions of the elongated object(s) 101 are oscillating. If the distal portions are oscillating about a value (S306=Yes), the process of FIG. 3A ends since oscillation about a value will confirm that the metric is at an extreme or within a predetermined range of the extreme. If the metric for the distal portions of the elongated object(s) 101 are not oscillating about a value, the system controller 150 commands the robotic device 160 via PID velocity control to rotate the elongated object(s) 101 in order to bring the metric to an extreme by returning to S302.

The process of FIG. 3A is based on obtaining a fluoroscopic image at each orientation angle and then analyzing the distal portion of the elongated object(s) 101 in each fluoroscopic image. The system controller 150 follows a control loop in the method of FIG. 3A, until the metric reaches an extreme or is brought within a predetermined range of an extreme. The control loop starts by setting the imaging system 170 to have a view parallel to the main axis of the main branch of the anatomy, which should be parallel to the main axis of the elongated object(s) 101, and then aligning the distal portion of the elongated object(s) 101 using radius of curvature or another metric as a shape metric. In FIG. 3B, robot control is shown to maximize the radius of curvature to align the elongated object(s) 101 in the plane of the view of the imaging system 170. Once aligned, the elongated object(s) 101 may be translated so that the distal portion points in the direction of the target vessel to increase chances of cannulation when the inner object of the elongated object(s) 101 (e.g., the guidewire) is advanced. Shape sensing hardware may be, but is not necessarily, used to sense the shape of the elongated object(s) 101 in the method of FIG. 3A.

In FIG. 3A and FIG. 3B, fluoroscopy images are repeatedly collected, and the elongated object(s) 101 segmentation is performed to parametrize the elongated object(s) 101 in the images. The segmentation may obtain, for example, a line segment representation, and may be based on artificial intelligence. The metric used to identify the optimums orientation angle may be the radius of curvature (in pixels) of the distal section of the elongated object(s) 101, and this metric may be maximized to identify the optimum orientation angle. Curvature is the smallest at the highest radius when the hooked distal end(s) of one or both elongated object(s) 101 is/are in the plane parallel to that of the imaging system 170. The robotic device 160 is controlled to rotate the elongated object(s) 101 until maximum radius of curvature is found, such as when the servo loop oscillates around a maximum value as confirmed at S306 (S306=Yes). When the center of the curve is facing away from the target vessel, the elongated object(s) 101 are rotated until the center of the curvature crosses the main axis of the elongated object(s) 101 and is on the same side of the axis as the target vessel.

Figure 3C:
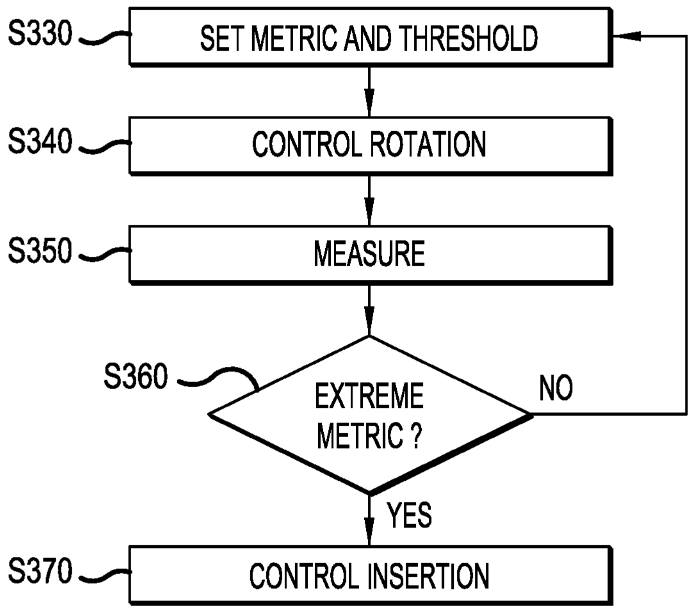
FIG. 3C illustrates another method for control of robotic endovascular devices to align to target vessels with fluoroscopic feedback, in accordance with a representative embodiment.

FIG. 3C illustrates another method for control of robotic endovascular devices to align to target vessels with fluoroscopic feedback, in accordance with a representative embodiment.

In FIG. 3C, the method starts by setting a metric and a threshold at S330. The metric may be a radius of curvature to be maximized, or another characteristic of curvature which is to be minimized. Other metrics may be set, as described with respect to other embodiments herein.

At S340, rotation of the elongated object(s) 101 is controlled. The system controller 150 may control the robotic device 160 to drive one or both of the elongated object(s) 101 to rotate about a main longitudinal axis of a first elongated device among the elongated object(s) 101. The rotation may be controlled to each of a plurality of orientation angles.

At S350, the metric of the first elongated device is measured. The metric is measured at each of the plurality of orientation angles until the extremity is identified. At S350, the image data from the imaging system 170 is analyzed to measure the metric. The image data may be analyzed by the system controller 150, and specifically by the processor 152 executing instructions from the memory 151 to analyze the image data. The measuring at S350 may be preceded by segmenting the elongated object(s) 101 in the image, and/or analyzing the image data to measure geometric characteristics of either or both of the outer device and the inner device among the elongated object(s) 101 in the image. The geometric characteristics may include one or metric(s) as described herein for various embodiments.

At S360, the method of FIG. 3C includes identifying an optimum orientation angle at which the metric is an extreme among the plurality of orientation angles. If the metric is not at an extreme at any particular orientation angle (S360=No), the process returns to S340. Otherwise (S360=Yes), the rotation ends and the controller controls insertion of the elongated object(s) 101 into the target branch at the identified optimum orientation angle, without retraction.

The method of FIG. 3C may be performed by the system 100, and primarily by the system controller 150 controlling the robotic device 160 using the image data received from the imaging system 170. The robotic device 160 is controlled to drive the elongated object(s) 101 in one or more degrees of freedom.

Control methods described herein may use fluoroscopic feedback to robotically and autonomously control a coaxial catheter and guidewire combination for the purpose of assisting in vascular navigation. Individual navigation steps may be broken down to discrete maneuvers/motions, which can be executed independently by an operator. For example, an operator may press a joystick button as the fourth interface 159. As a result, an operator is provided an ability to execute high level maneuvers/motions without having to explicitly control each minute motion of the elongated object(s) 101.

Figure 4:
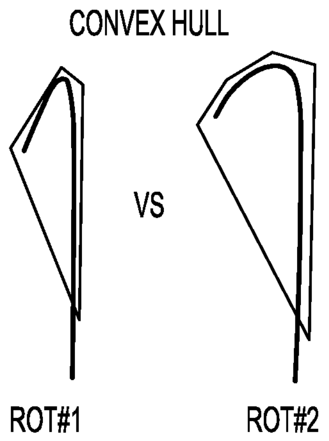
FIG. 4 illustrates another sequence of motions and a metric to align a catheter with a target vessel for cannulation, in accordance with a representative embodiment.

FIG. 4 illustrates another sequence of motions and a metric to align a catheter with a target vessel for cannulation, in accordance with a representative embodiment.

In FIG. 4, an area of the convex hull serves as a metric corresponding to a minimal convex shape corresponding to the distal end of the elongated object(s) 101. The area of a convex hull increases when the elongated object(s) 101 is/are in the plane parallel with the image plane of the imaging system 170, and this in turn will reflect that the elongated object(s) 101 are at the optimum orientation angle for insertion into the target branch. The area of the convex hull is observable from the X-ray images from the imaging system 170.

Other metrics may also be used to identify the optimum orientation angle for the distal tip of one or both of the elongated object(s) 101. For example, a maximum arc length of the visible distal tip of the elongated object(s) 101 reflects when the elongated object(s) 101 are in a plane parallel with the detector plane. Accordingly, the maximum arc length may serve as the metric to be measured. Additionally, maximum tangent angle(s) of the distal tip(s) of the elongated object(s) 101 is/are aligned with the view when the tangent section of the distal tip(s) of the elongated object(s) 101 is/are angled maximally towards the perpendicular of the main axis of the elongated object(s) 101. Accordingly, the maximum tangent angle(s) may serve as the metric to be measured. Moreover, a maximum tip distance, defined as when the tip distance from the distal tip to the main axis of the elongated object(s) 101 is/are at maximum, may reflect that the elongated object(s) are aligned with the view when considering this metric among different orientation angles. Accordingly, the maximum tip distance may serve as the metric to be measured. Similarly, eigenvalue of the second eigenvector, representing the variation of the device shape variability, may reflect that the elongated object(s) are aligned with the view when considering this metric among different orientation angles.

In some embodiments, an out of plane target may be aligned. For example, when cannulation requires viewing where the target vessel is perpendicular to the plane of the imaging system 170, it may be desirable to minimize a metric. Ambiguity may be addressed with a priori knowledge of the orientation of the vessel and direction of initial rotation of the elongated object(s), so that the out of plane target is aligned.

In some embodiments, a projection of the elongated object(s) 101 may be estimated, so that alignment can be made with a current view which is out-of-plane with the trajectory of the projection. When the shape of the elongated object(s) 101 is stiff, the projection view of the elongated object(s) 101 can be used as a template upon which the robotic device 160 is driven, after the projection view is registered with the current shape of the elongated object(s) 101.

Figure 5:
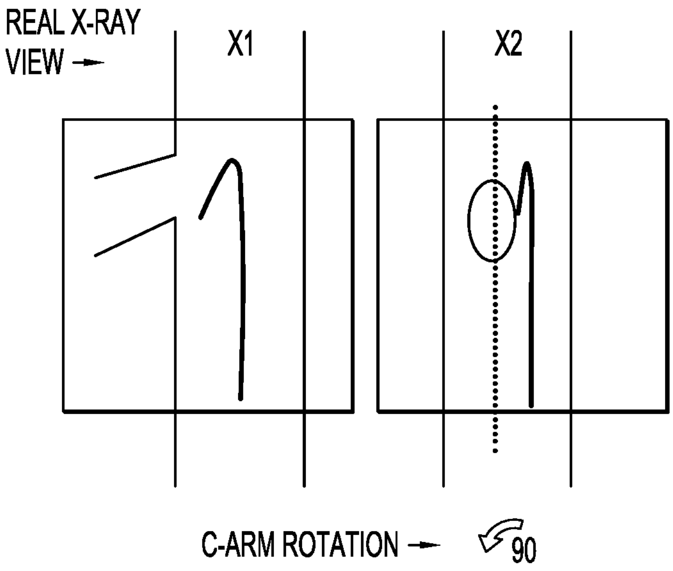
FIG. 5 illustrates a sequence of motions to align a catheter with a target vessel for cannulation based on corresponding X-ray views, in accordance with a representative embodiment.

FIG. 5 illustrates a sequence of motions to align a catheter with a target vessel for cannulation based on corresponding X-ray views, in accordance with a representative embodiment.

Once the elongated object(s) 101 is/are aligned in a first view, the image plane of the imaging system 170 may be moved to an orthogonal view so that the target branch axis is perpendicular to the image plane of the imaging system 170. The alignment may then be refined in the orthogonal view. In the embodiment of FIG. 5, the distance of the tip of the elongated object(s) 101 to the axis parallel to the main axis of the elongated object(s) 101 is minimized. In this embodiment, the driving of the elongated object(s) 101 is based on two consecutive views of the imaging system 170. Once aligned, the elongated object(s) 101 may be driven/translated, wherein the alignment improves the cannulation.

Once the view of the elongated object(s) is aligned, the motion of the elongated object(s) 101 is linear in one degree of freedom to align the tangential trajectory of the distal section of the elongated object(s) 101 with the target vessel for cannulation with a guidewire.

In some embodiments, the alignment may be coordinated with the frame rate of the imaging system 170. In these embodiments, to reduce radiation exposure, the incremental motion of the elongated object(s) 101 motion may be synchronized with the fluoroscopy. For example, the elongated object(s) 101 may be rotated 15 degrees, an update fluoroscopy may be taken, the elongated object(s) 101 may be rotated another 15 degrees, and so on. In some embodiments, the system controller 150 may command the imaging system 170 to oscillate back and forth between the two views to iteratively complete the cannulation.

In some embodiments, the target vessel may be selected on a user interface, such as on the display 180 or via the fourth interface 159. For example, a user may use a touchscreen or a cursor to point and click on the target vessel. The system controller 150 then calculates the plane of the desired target vessel and a C-arm position of the imaging system 170 is suggested. The user confirms the plane and the C-arm position to move the C-arm, and the robotic device 160 moves to align the elongated object(s) 101 with that target vessel in the corresponding view. To facilitate selecting target vessels, a suggestion mechanism may be provided based on the location of the distal section of the elongated object(s) 101 relative to the upcoming bifurcation. The next bifurcation may be automatically made the primary selection and require only an acknowledgement for triggering the alignment maneuver.

In some embodiments, alignment may be combined with open-loop control. For example, to minimize usage of X-ray imaging, open-loop control may be used initially by estimating the current curvature from 2D X-ray projections, and comparing the estimated current curvature to an expected minimum curvature. Precision may be made possible with end-point sensing, such as by using X-ray feedback.

In some embodiments, collimation around a distal dip of the elongated object(s) 101 may be employed. Since maneuvers are performed semi-automatically, the area around the elongated object(s) 101 is the region required for feedback. Synchronization of collimation during servo-driven motions may be performed based on segmenting the elongated object(s) 101 that is/are to be controlled, and a bounding box of the distal section(s) to be controlled is created.

In some embodiments, biplane X-ray imaging may be employed for the alignment. When biplane imaging is employed, the target reference datum may be defined in 3D using triangulation. The tip of the elongated object(s) 101 may be continuously triangulated using standard point epipolar geometry, as in stereo vision techniques. When the two X-ray imaging sources are not calibrated relative to each other, independent target references may be used, and the system controller 150 may require meeting each of the target references independently for the goal to be reached.

Figure 6:
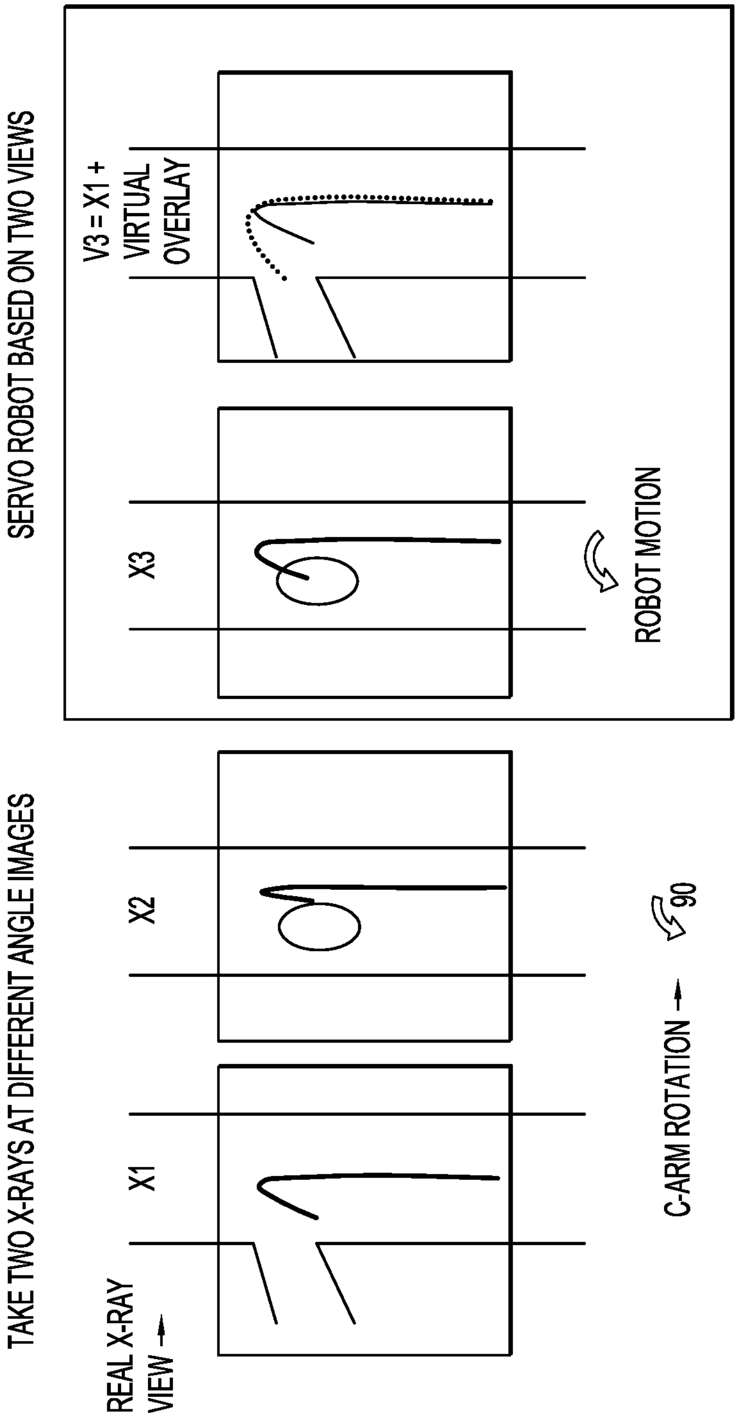
FIG. 6 illustrates virtual-image based control of robotic endovascular devices to align to target vessels with fluoroscopic feedback, in accordance with a representative embodiment.

FIG. 6 illustrates virtual-image based control of robotic endovascular devices to align to target vessels with fluoroscopic feedback, in accordance with a representative embodiment.

When the imaging system 170 is a monoplane imaging system, the lack of depth information in resultant images may make tasks such as cannulating a vascular branch challenging not only for a human user (with or without robotic aid) but also for an automated robotic system such as the combination of the robotic device 160 and the system controller 150. In embodiments based on FIG. 6, the system controller 150 may be provided with an estimate of the elongated object(s) 101 in a second visualization plane (or biplane). The estimation of a biplane view from a single 2D projection image may reflect ambiguities. However, using a time-series of two-dimensional fluoroscopic imaging data synchronized with the servo control provided by the robotic device 160 and the system controller 150, the ambiguities may be resolved for endovascular navigation using the elongated object(s) 101*s*. In FIG. 6, two different perspective X-ray images are first taken of the target vessel (X1, X2). Then a secondary virtual image (X3–X1+Virtual Overlay) is synthesized from a third image (X3) and the position of the elongated object(s) 101 in the two initial images. The two image feeds may then be used for virtual-image based control of the robotic device 160 to drive the elongated object(s) 101.

Figure 7:
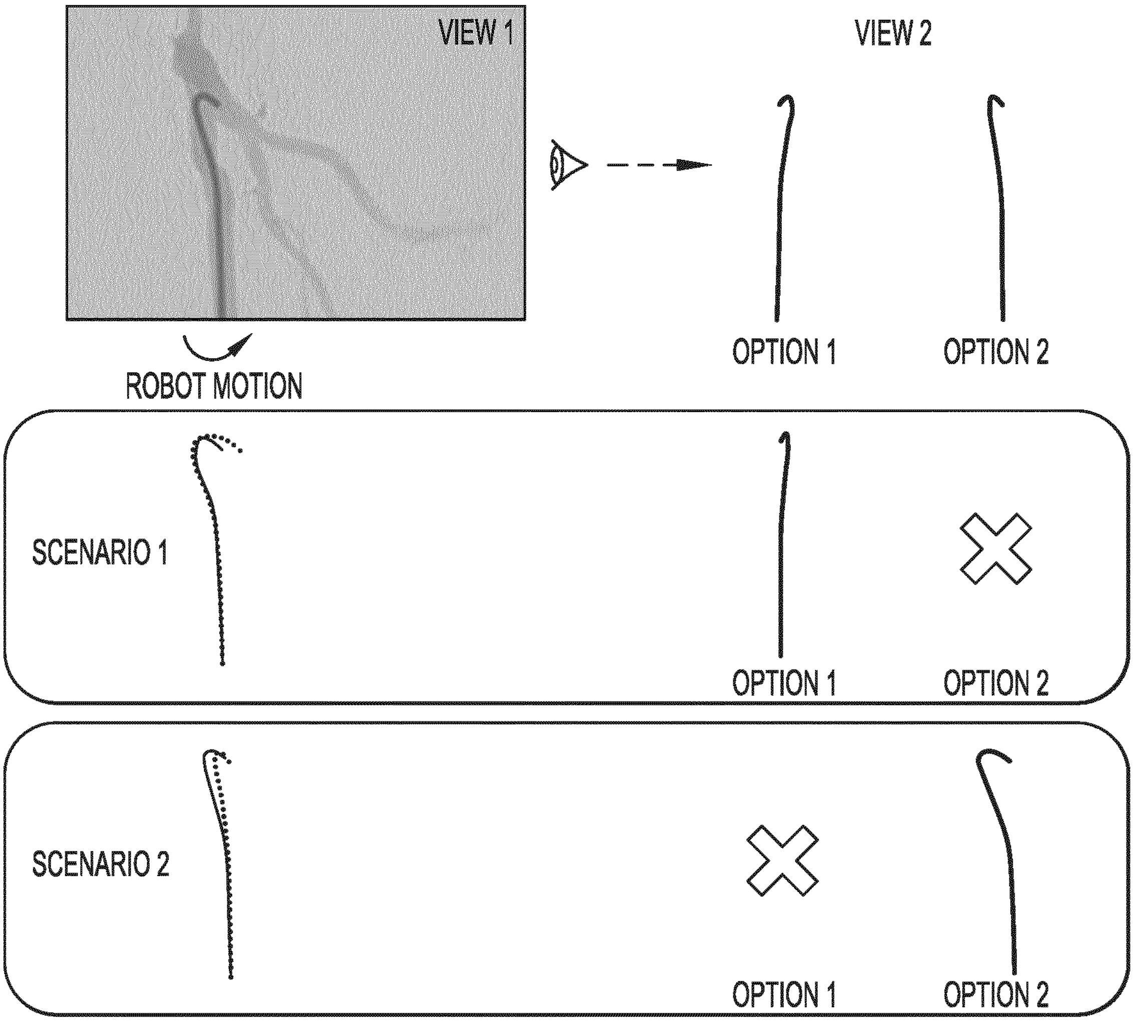
FIG. 7 illustrates machine-learning based disambiguation for control of robotic endovascular devices to align to target vessels with fluoroscopic feedback, in accordance with a representative embodiment.

FIG. 7 illustrates machine-learning based disambiguation for control of robotic endovascular devices to align to target vessels with fluoroscopic feedback, in accordance with a representative embodiment.

As an example, FIG. 7 shows ambiguities in the elongated object(s) 101 configuration and orientation that may arise in biplane estimation from a single 2D projection image of the elongated object(s) 101. That is, just from view 1, it is unclear whether the elongated object(s) 101 is pointing anteriorly, which would result in the biplane view (view 2) shown in option 1, or posteriorly, which would result in the view shown in option 2. With time-series information along with some expectation of the direction that the elongated object(s) 101 should move in, this ambiguity can be resolved. The expectation of the direction the elongated object(s) 101 should move in is known to the system controller 150.

In FIG. 7, biplane estimation of the elongated object(s) contains ambiguities when based on a single 2D projection image. However, with time-series sequences of two-dimensional projection images coupled with input from the system controller 150, machine learning models may be trained to disambiguate the biplane estimate of the elongated object(s) and predict the shape of the elongated object(s) in this secondary view. With this improved understanding of how the elongated device(s) are oriented, the system controller 150 may make improved estimates of movements to be applied to complete particular tasks such as cannulating a vessel.

For example, the system 100 may expect the distal end of the elongated object(s) 101 to rotate toward the posterior direction when a fluoroscopy image sequence is available as the robotic device 160 applies an inward rotation to the elongated object(s) 101. Observations in the image sequence may be used to determine the configuration of the elongated object(s) 101 in the biplane view. For instance, in scenario 1 in FIG. 7, as the elongated object(s) 101 is moved posteriorly, the distal part of the elongated object(s) 101 appear larger in view 1 as shown by the dotted line. This means that the curve in the distal part of the elongated object(s) 101 is now almost perpendicular to the viewing direction, and implies that prior to the application of the rotation to the elongated object(s) 101, the elongated object (s) 101 must be pointing anteriorly. This may be used to confirm that the elongated object(s) 101 is in the configuration shown in option 1 in the biplane view and option 2 can be ruled out.

Similarly, if the application of the rotation toward the posterior direction results in the distal part of the elongated object(s) 101 appearing smaller in view 1 (FIG. 7, scenario 2), this implies that the elongated object(s) 101 must be facing posteriorly to begin with and further rotation in that direction caused the distal part of the elongated object(s) 101 to be oriented parallel to the viewing direction. This confirms that the elongated object(s) 101 is in the configuration shown in option 2 in the biplane view.

Figure 8:
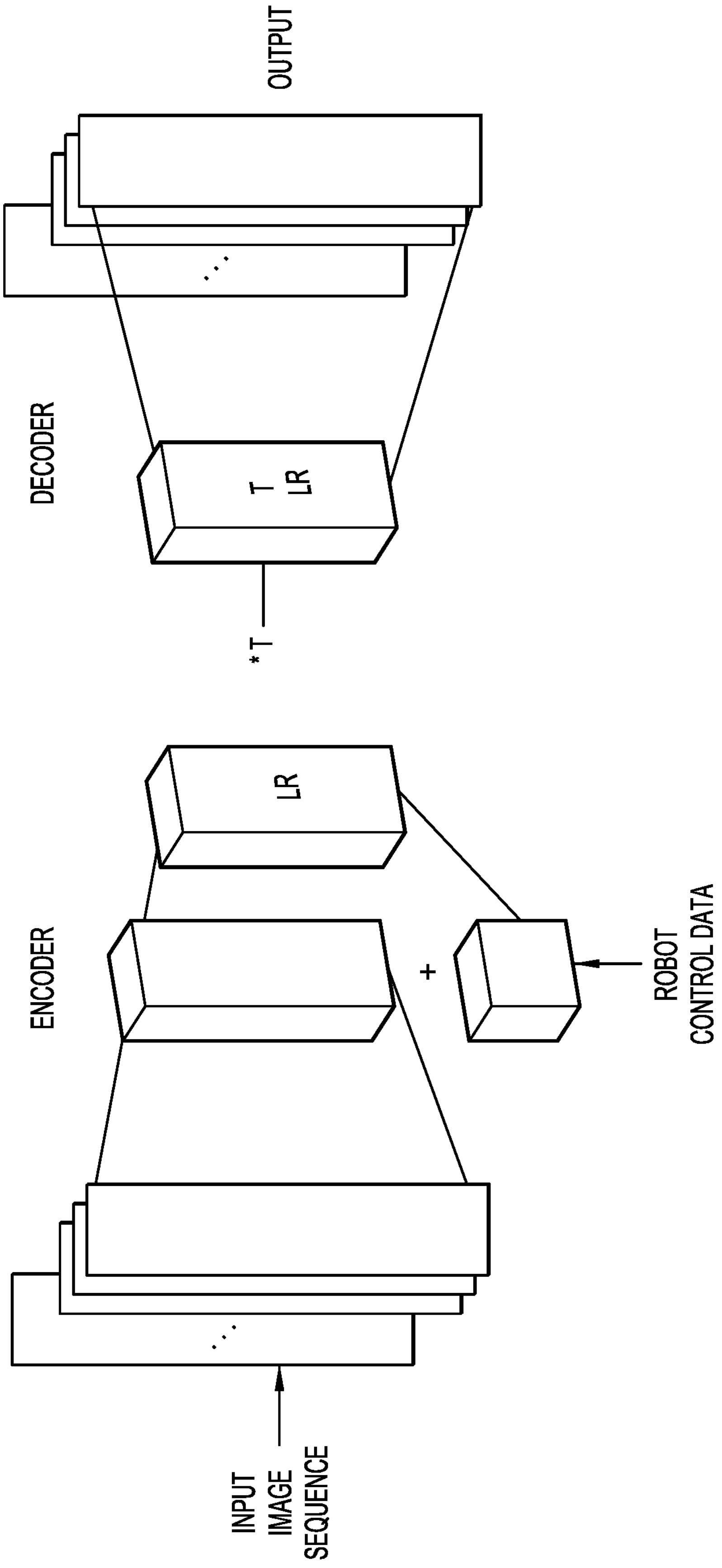
FIG. 8 illustrates machine-learning based control of robotic endovascular devices to align to target vessels with fluoroscopic feedback, in accordance with a representative embodiment.

FIG. 8 illustrates machine-learning based control of robotic endovascular devices to align to target vessels with fluoroscopic feedback, in accordance with a representative embodiment.

Machine learning models such as transforming autoencoders and other neural network (NN) architectures can be trained to learn the space of 3D shapes that the elongated object(s) 101 can attain and, therefore, estimate the shape of the elongated object(s) 101 in the biplane view up to the ambiguity if only a single 2D image is provided. With a time-series sequence of two-dimensional projection images and synchronized input from the system controller 150, models can be trained to disambiguate the biplane view of the elongated object(s) 101. For instance, a modified transforming autoencoder network may be used to input a sequence of fluoroscopy images (or a segmentation of the coordinates of the elongated object(s) 101) into an encoder such as an RNN encoder) and the synchronized information for the system controller 150 such as rotation angle can be concatenated to a hidden representation of the input learned by the encoder. The final latent representation (LR) captures the evolution of the elongated object(s) 101 through the fluoroscopy frames and the input from the robotic device 160 that caused the evolution of the elongated object(s) 101. This learned representation is transformed by the known transformation, T, between the live viewing angle and the desired biplane view. The transformed representation (TLR) may then be decoded into images of the elongated object(s) 101 in the biplane view. During training, the output may be compared to ground truth of the shape of the elongated object(s) 101 in the biplane view. Ground truth may be acquired using a biplane imaging system or using shape sensed devices that generate the 3D shape of the device, which can be projected onto view 1 and the biplane view. Comparison between the output and the ground truth shape of the elongated object(s) 101 in the biplane view may be performed using any loss function including the mean absolute error (or L1 norm), the mean squared error, the root mean squared error (or L2 norm), the negative log-likelihood loss, and so forth. During training, the value of the loss function is typically minimized over several iterations by adjusting the parameters of the NN (including the encoder and decoder components in the case of the transforming autoencoder) such that the output of the NN more closely matches the ground truth. The minimization of the loss function through the adjusting of NN parameters, including NN weights and biases, may be performed using any method including stochastic gradient descent, batch gradient descent, mini-batch gradient descent, Gauss-Newton, Levenberg Marquardt, Momentum, Adam, and so forth. These methods compute the derivative of the loss function with respect to the model parameters using the chain rule in a process called backpropagation, where derivatives are computed starting at the last layer or output layer, moving toward the first layer or input layer. These derivatives inform the algorithm how the model parameters must be adjusted in order to minimize the loss function. The training starts with the NN parameters initialized to random values in the first training iteration, which results in inaccurate outputs. Using backpropagation, the NN parameter values are adjusted at each iteration, resulting in iterative improvements in output. Training is terminated when some termination criteria are met (e.g., the difference between the output and ground truth is within an acceptable range for the training data or for some validation data, a large number of training iterations has been performed, or other criteria of termination determining the end of the process).

With sufficient data, the models specific to the elongated object(s) 101 can be trained to capture the space of configurations that the elongated object(s) 101 can attain in different views. The control data for controlling the robotic device 160 is the disambiguating factor between the configurations of the elongated object(s) 101 that can be obtained in the biplane view. The methods based on FIG. 7 and FIG. 8 can be applied to biplane views at any angle offset, T, from view 1. The trained NN makes predictions on new input data using the trained values of its parameters. If the training process is successful, the trained NN accurately predicts the output from the new input data. Additionally, the methods based on FIG. 7 and FIG. 8 can also be used to estimate how the elongated object(s) 101 is evolving in an old view if the angle of the C-arm of the imaging system 170 is changed and a new image is acquired before the elongated object(s) 101 manipulation is continued. With a live view and an estimated view of the elongated object(s) 101, the system controller 150 can better estimate movements that must be applied to the elongated object(s) 101 to complete tasks such as cannulating a vessel.

FIG. 9 illustrates a computer system, on which a method for control of robotic endovascular devices to align to target vessels with fluoroscopic feedback is implemented, in accordance with another representative embodiment.

Referring to FIG. 9, the computer system 900 includes a set of software instructions that can be executed to cause the computer system 900 to perform any of the methods or computer-based functions disclosed herein. The computer system 900 may operate as a standalone device or may be connected, for example, using a network 901, to other computer systems or peripheral devices. In embodiments, a computer system 900 performs logical processing based on digital signals received via an analog-to-digital converter.

In a networked deployment, the computer system 900 operates in the capacity of a server or as a client user computer in a server-client user network environment, or as a peer computer system in a peer-to-peer (or distributed) network environment. The computer system 900 can also be implemented as or incorporated into various devices, such as a workstation that includes the system controller 150 in FIG. 1A, a stationary computer, a mobile computer, a personal computer (PC), a laptop computer, a tablet computer, or any other machine capable of executing a set of software instructions (sequential or otherwise) that specify actions to be taken by that machine. The computer system 900 can be incorporated as or in a device that in turn is in an integrated system that includes additional devices. In an embodiment, the computer system 900 can be implemented using electronic devices that provide voice, video or data communication. Further, while the computer system 900 is illustrated in the singular, the term "system" shall also be taken to include any collection of systems or sub-systems that individually or jointly execute a set, or multiple sets, of software instructions to perform one or more computer functions.

As illustrated in FIG. 9, the computer system 900 includes a processor 910. The processor 910 may be considered a representative example of the processor 152 of the system controller 150 in FIG. 1B and executes instructions to implement some or all aspects of methods and processes described herein. The processor 910 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 910 is an article of manufacture and/or a machine component. The processor 910 is configured to execute software instructions to perform functions as described in the various embodiments herein. The processor 910 may be a general-purpose processor or may be part of an application specific integrated circuit (ASIC). The processor 910 may also be a microprocessor, a microcomputer, a processor chip, a controller, a microcontroller, a digital signal processor (DSP), a state machine, or a programmable logic device. The processor 910 may also be a logical circuit, including a programmable gate array (PGA), such as a field programmable gate array (FPGA), or another type of circuit that includes discrete gate and/or transistor logic. The processor 910 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 900 further includes a main memory 920 and a static memory 930, where memories in the computer system 900 communicate with each other and the processor 910 via a bus 908. Either or both of the main memory 920 and the static memory 930 may be considered representative examples of the memory 151 of the system controller 150 in FIG. 1B, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 920 and the static memory 930 are articles of manufacture and/or machine components. The main memory 920 and the static memory 930 are computer-readable mediums from which data and executable software instructions can be read by a computer (e.g., the processor 910). Each of the main memory 920 and the static memory 930 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, Blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 900 further includes a video display unit 950, such as a liquid crystal display (LCD), an organic light emitting diode (OLED), a flat panel display, a solid-state display, or a cathode ray tube (CRT), for example. Additionally, the computer system 900 includes an input device 960, such as a keyboard/virtual keyboard or touch-sensitive input screen or speech input with speech recognition, and a cursor control device 970, such as a mouse or touch-sensitive input screen or pad. The computer system 900 also optionally includes a disk drive unit 980, a signal generation device 990, such as a speaker or remote control, and/or a network interface device 940.

In an embodiment, as depicted in FIG. 9, the disk drive unit 980 includes a computer-readable medium 982 in which one or more sets of software instructions 984 (software) are embedded. The sets of software instructions 984 are read from the computer-readable medium 982 to be executed by the processor 910. Further, the software instructions 984, when executed by the processor 910, perform one or more steps of the methods and processes as described herein. In an embodiment, the software instructions 984 reside all or in part within the main memory 920, the static memory 930 and/or the processor 910 during execution by the computer system 900. Further, the computer-readable medium 982 may include software instructions 984 or receive and execute software instructions 984 responsive to a propagated signal, so that a device connected to a network 901 communicates voice, video or data over the network 901. The software instructions 984 may be transmitted or received over the network 901 via the network interface device 940.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, control of robotic endovascular devices to align to target vessels with fluoroscopic feedback enables automatic and consistent wire manipulation assistance. The wire manipulation assistance may reduce risks in medical interventions. An example of the risks reduced by the subject matter described herein include the risk of perforating delicate vascular walls, which may result in fatal complications. Another example of the risks reduced by the subject matter described herein include the risks presented by stroke treatment (thrombectomy), where timely treatment by skilled professional is essential but not always available. In another example, precise cannulation of an ostium in a fenestrated graft implant may be performed using the teachings herein during endovascular repair of an abdominal aortic aneurysm.

As set forth above, endovascular intervention workflow may be improved by enabling automatic navigation to deposit an intravascular device into a vascular branch. The elongated object(s) 101 may be aligned to be parallel to the imaging view with real-time image feedback to facilitate branch cannulation. The automated navigation may be achieved with fluoroscopic imaging synchronized with servo control of the elongated object(s) 101.

Although control of robotic endovascular devices to align to target vessels with fluoroscopic feedback has been described with reference to several exemplary embodiments, it is understood that the words that have been used are words of description and illustration, rather than words of limitation. Changes may be made within the purview of the appended claims, as presently stated and as amended, without departing from the scope and spirit of control of robotic endovascular devices to align to target vessels with fluoroscopic feedback in its aspects. Although control of robotic endovascular devices to align to target vessels with fluoroscopic feedback has been described with reference to particular means, materials and embodiments, control of robotic endovascular devices to align to target vessels with fluoroscopic feedback is not intended to be limited to the particulars disclosed; rather control of robotic endovascular devices to align to target vessels with fluoroscopic feedback extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

In particular, the invention is not limited to the use of catheter or guidewire, but can be clearly implemented with any kind of elongated device(s), especially elongated devices provided with an asymmetry with respect to the longitudinal axis of the device(s) which can be used for determining a metric according to the invention when rotating, rolling this device. Such devices may be (without any limitation whatsoever) implants, imaging (e.g. IVUS—intravascular ultrasound) devices, atherectomy devices, notched catheters, beveled catheters/needles, ballons, stents, or other medical elongated instrument.

In particular, metric used in this invention is not limited to determination of a radius of curvature of a distal section of one of the elongated device(s) (or object(s)), but could be any other metric, especially metric representative of the out-of-plane angle between the device plane and the image plane. Here are examples of metrics which can be used as alternatives or in combination with the radius of curvature or with other metric(s):

- distance from the main longitudinal axis of the device to the centroid of the shape of a distal non-linear section of the device (e.g. a curved tip); the main longitudinal axis can be a centerline determined from image data related to the device, or extracted using PCA (principle component analysis) to define this longitudinal axis;
- distance from the main longitudinal axis of the device to a feature of the shape of a distal non-linear section of the device (e.g., a bead, a unique trackable shape such as an apex);
- a surface area of the profile of the end section of the device (or the tip of it), which can be minimized or maximized when the device is rotated (e.g. rotating the device until the larger area side-profile is viewed—i.e. maximum surface area. Alternatively or in combination, the rotation of the device could be implemented until the visible surface area is minimized—the smaller area profile is roughly perpendicular to the image plane)
- a ratio between the two PCA pixel data points along the main longitudinal device ("major" data points) and PCA pixel data points (fewer) among minor axes, which reflects a specific orientation of the device (an ellipse should be widest when aligned). This method is for instance know in Model-Based Machine Learning (Early Access): Chapter 8 "How to Read a Model (mbmlbook.com)", section 8.3 (Model-Based Machine Learning (Early Access): Chapter 8. How to Read a Model (mbmlbook.com—https://www.mbmlbook.com/ModelAnalysis_Principal_Component_Analysis.html)
- when an anatomical feature is visible in the image (e.g. the ostium of a branched lumen), the metric could be also calculation of the distance of a point of the device (e.g. the tip) to this anatomical feature when the device is rotated;
- if the terminal portion of the device is linearly angled (i.e. not curved) or has a linearly angled feature (e.g., bevel tip of a needle), the metric can be the largest acute angle from the main longitudinal axis.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A system controller for controlling a robotic device to drive motion of a first elongated device relative to a targeted vessel, the system controller comprising:

an image interface that receives data of: a two-dimensional x-ray image and the first elongated device in the two-dimensional x-ray image; and a processor in communication with the memory, the processor configured to:

control rotation of the first elongated device about a main longitudinal axis of the first elongated device at a plurality of orientation angles, measure, from the data, a metric of the first elongated device at each of the plurality of orientation angles, the metric being representative of an out-of-plane angle defined by the angle between a plane defined by the first elongated device and the plane of the image, identify at least one extreme orientation angle at which the metric is an extreme among the plurality of orientation angles, and control movement of the first elongated device at an optimum orientation angle of the first elongated device determined from an identified extreme to enter into or to face the targeted vessel.

2. The system controller of claim 1, wherein the processor is further configured to:

position an imaging system that captures the two-dimensional x-ray image to capture the two-dimensional x-ray image such that a plane of the two-dimensional x-ray image lies in a cross-section of an entrance of the targeted vessel.

3. The system controller) of claim 1, wherein the processor is further configured to:

position an imaging system that captures the two-dimensional x-ray image such that a plane of the two-dimensional x-ray image is perpendicular to a cross-section of an entrance of the targeted vessel.

4. The system controller of claim 1, wherein the processor is further configured to determine an optimum orientation angle that corresponds to an identified extreme.

5. The system controller of claim 1, wherein the processor is further configured to select an orientation angle at which the out-of-plane angle is smallest.

6. The system controller of claim 1, wherein the first elongated device comprises a distal end that directionally diverges from the main longitudinal axis, and the metric corresponds to an orientation of the distal end.

7. The system controller of claim 1, wherein the robotic device is configured to drive motion of the first elongated device and a second elongated device which is coaxial with the first elongated device.

8. The system controller of claim 7, wherein, after the first elongated device is positioned at the optimum orientation angle, the processor is configured to maneuver the second elongated device to the targeted vessel.

9. The system controller of claim 8, wherein the processor is further configured to maneuver the first elongated device into the targeted vessel.

10. The system controller of claim 1, wherein the processor is further configured to drive motion of the first elongated device towards a portion of the targeted vessel which is an entrance to the targeted vessel, and wherein the targeted vessel is branched.

11. The system controller of claim 1, wherein the processor is further configured to perform an image segmentation of the two-dimensional x-ray image such that the first elongated device is identified in the two-dimensional x-ray image through segmentation.

12. The system controller of claim 1, wherein the processor is further configured to automatically align a tip of the first elongated device with an entrance of the targeted vessel, without retracting or advancing the first elongated device.

13. The system controller of claim 1, wherein the metric comprises a geometric characteristic of a distal portion of the first elongated device relative to the main longitudinal axis of the first elongated device.

14. The system controller of claim 13, wherein the geometric characteristic of the distal portion comprises a minimal convex shape encompassing the distal portion in the two-dimensional x-ray image.

15. The system controller of claim 1, wherein the processor is further configured to use a trained machine learning model to disambiguate a biplane estimate of the first elongated device and predict a shape of the first elongated device in a secondary plane using a time-series sequences of two-dimensional projection images and synchronized input from the system controller including rotation angle information to control rotation of the first elongated device.

16. The system controller of claim 1, wherein the processor is further configured to maneuver the first elongated device into the targeted vessel using servo control.

17. The system controller of claim 1, wherein the processor is further configured to control the robotic device to rotate the first elongated device automatically until a distal end of the first elongated device is parallel to the two-dimensional x-ray image.

18. A system, comprising:

an X-ray imaging system configured to image anatomy of a subject and a first elongated device;

a robotic device configured to control movement of the first elongated device; and a processor configured to:

control rotation of the first elongated device about a main longitudinal axis of the first elongated device at a plurality of orientation angles, measure, from images captured by the X-ray imaging system, a metric of the first elongated device at each of the plurality of orientation angles, the metric being representative of an out-of-plane angle defined by the angle between a plane defined by the first elongated device and the plane of the image, identify at least one extreme orientation angle at which the metric is an extreme among the plurality of orientation angles, and control movement of the first elongated device at an optimum orientation angle determined from an identified extreme to enter into or face a targeted vessel.

19. The system of claim 18, further comprising:

a display configured to display the images captured by the X-ray imaging system and the first elongated device in the images captured by the X-ray imaging system.

20. A method for controlling a robotic device to drive motion of a first elongated device relative to a targeted vessel, the method comprising:

receiving data of a two-dimensional x-ray image and of the first elongated device in the two-dimensional x-ray image;

controlling rotation of the first elongated device about a main longitudinal axis of the first elongated device at a plurality of orientation angles;

measuring, from the data, a metric of the first elongated device at each of the plurality of orientation angles, the metric being representative of an out-of-plane angle defined by the angle between a plane defined by the first elongated device and the plane of the image;

identifying at least one extreme orientation angle at which the metric is an extreme among the plurality of orientation angles, identifying an optimum orientation angle from an identified extreme among the plurality of orientation angles for a movement of the first elongated device into or towards the targeted vessel, and controlling movement of the first elongated device at the optimum orientation angle to enter into or face the targeted vessel.

21. The method of claim 20, further comprising:

receiving encoded positional information from the robotic device;

determining a current encoded position of the robotic device based on the encoded positional information;

recalling images corresponding to the current encoded position from a previous sequence of images based on the current encoded position of the robotic device; and generating an estimated view of the first elongated device in a secondary plane based on the images corresponding to the current encoded position.

* * * * *